United States Patent [19]

Martin et al.

[11] Patent Number: 5,423,854
[45] Date of Patent: Jun. 13, 1995

[54] COELIOSCOPIC ANGULATION FORCEPS

[76] Inventors: Alain Martin, 128 Route de Corbiac, F-33160 Saint Medard en Jalles; Francois Dubecq-Princeteau, 91 rue Hoche, F-33000 Bordeaux, both of France

[21] Appl. No.: 99,343

[22] Filed: Jul. 30, 1993

[30] Foreign Application Priority Data

Jul. 31, 1992 [FR] France ................. 92 09742

[51] Int. Cl.6 .............................................. A61B 17/28
[52] U.S. Cl. ..................................... 606/205; 128/751
[58] Field of Search ............... 606/139, 142, 148, 170, 606/174, 205–210; 128/749, 751

[56] References Cited

U.S. PATENT DOCUMENTS

| | | | |
|---|---|---|---|
| 2,507,710 | 5/1950 | Grosso | 606/208 |
| 4,085,756 | 4/1978 | Weaver. | |
| 4,621,640 | 11/1986 | Mulhollan. | |
| 4,763,669 | 8/1988 | Jaeger | 606/170 |
| 4,872,456 | 10/1989 | Hasson. | |
| 5,192,298 | 3/1993 | Smith et al. | 606/205 |
| 5,254,130 | 10/1993 | Powcet et al. | 606/210 |
| 5,263,958 | 11/1993 | deGuillebon et al. | 606/170 |

FOREIGN PATENT DOCUMENTS

| | | | |
|---|---|---|---|
| 0306123 | 4/1988 | European Pat. Off. . | |
| 185025 | 3/1956 | Germany | 606/139 |
| 4104755 | 8/1992 | Germany | 606/170 |
| 2056898 | 3/1981 | United Kingdom . | |
| 980703 | 12/1982 | U.S.S.R. | 606/174 |
| 8911827 | 12/1989 | WIPO . | |

*Primary Examiner*—Stephen C. Pellegrino
*Assistant Examiner*—Nancy Mulcare
*Attorney, Agent, or Firm*—Roylance, Abrams, Berdo & Goodman

[57] ABSTRACT

A coelioscopic angulation forceps includes a tube, a pair of jaws at one tube extremity and a pair of control eyelets at the other tube extremity connected to the pair of jaws by an activation rod assembly housed in the tube. The pair of jaws is borne by a jaw holder head mounted and articulated onto the tube extremity around an axis perpendicular to that of the tube and is able to occupy two positions. In one position, the pair of jaws, in the rest position, is in prolongation of the tube. In the other position, the pair of jaws forms with the axis of the tube a specific angulation. The forceps also includes a device for controlling the positioning of the jaw holder head in either of the two positions and being able to be activated from the proximal extremity of the tube.

16 Claims, 5 Drawing Sheets

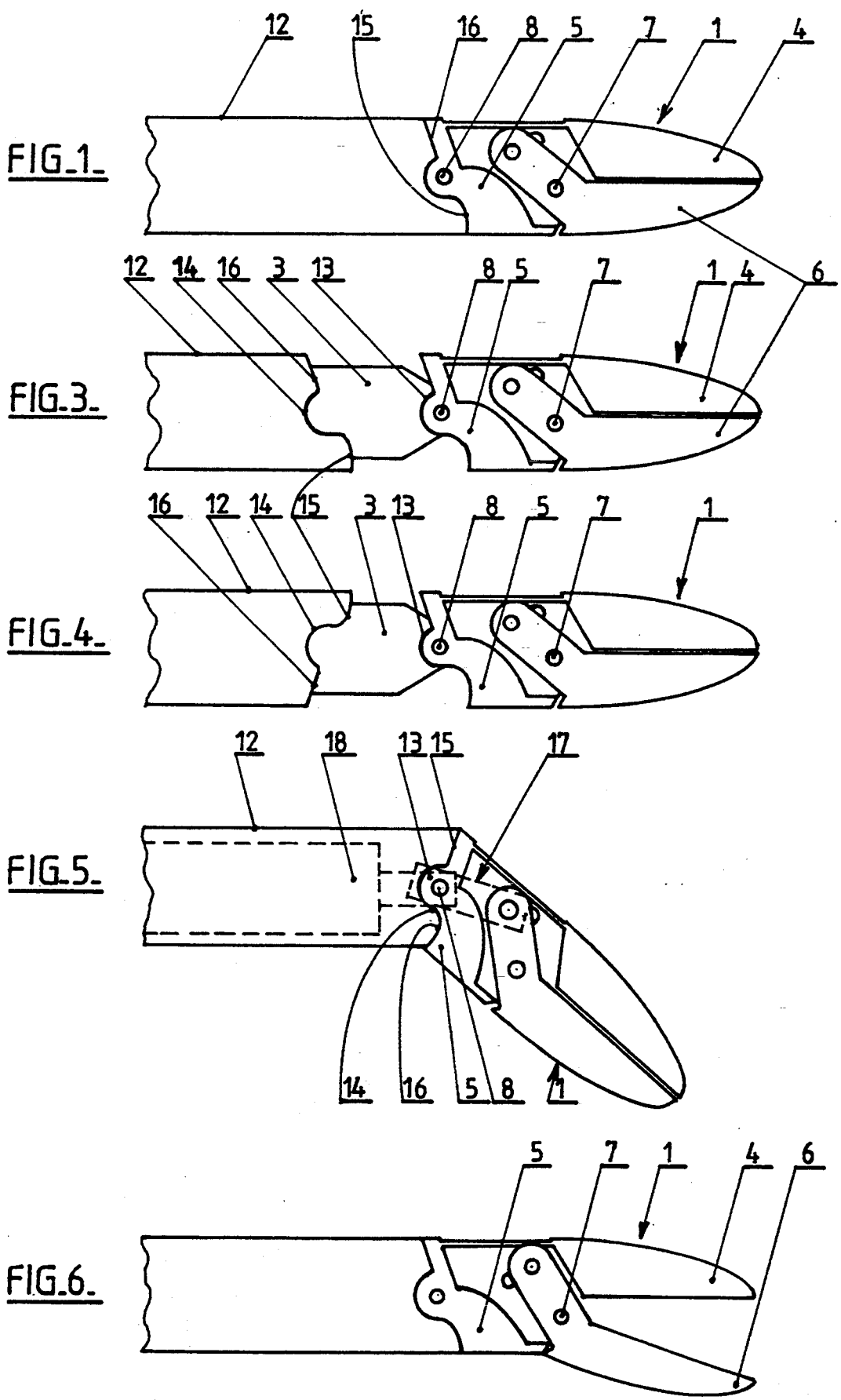

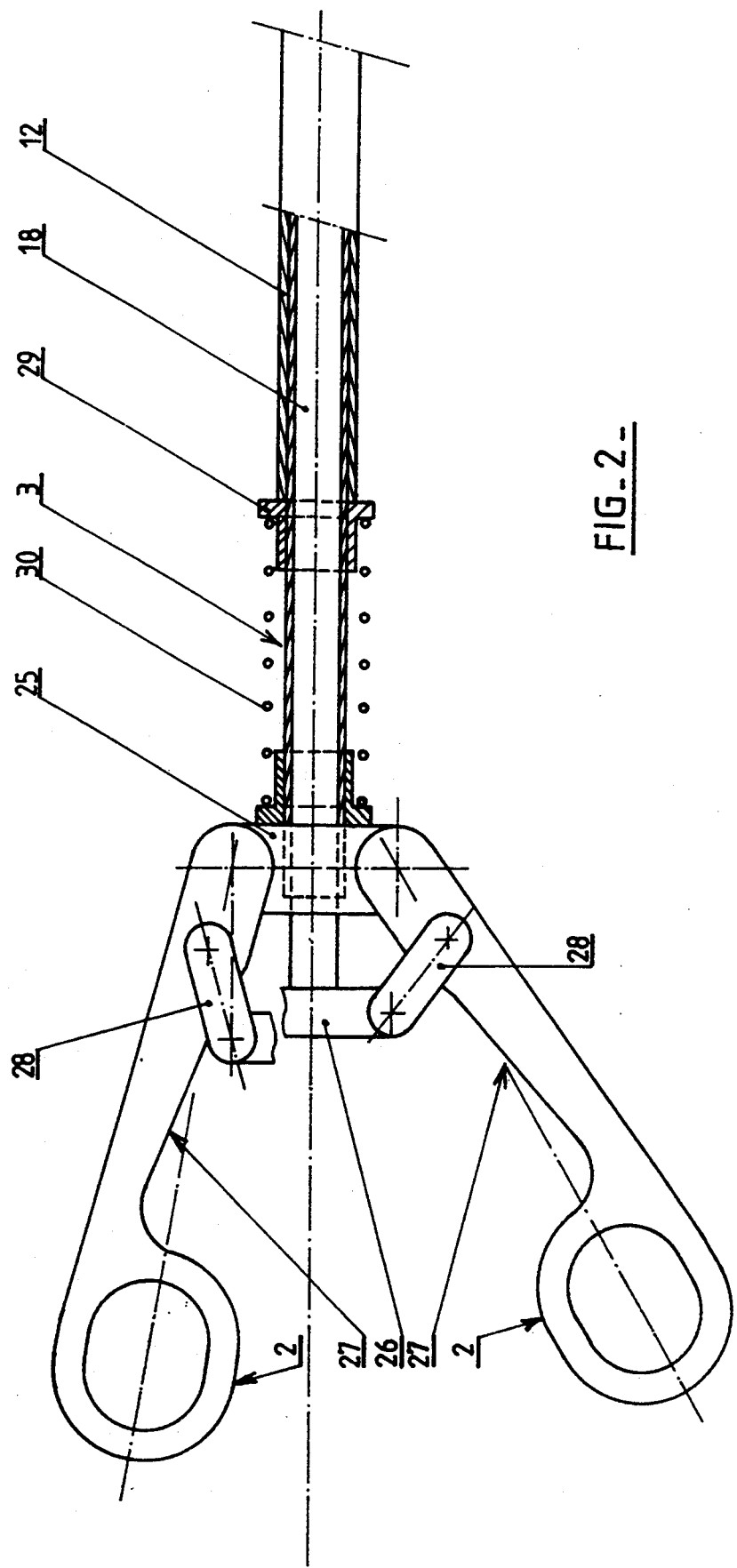
FIG._2_

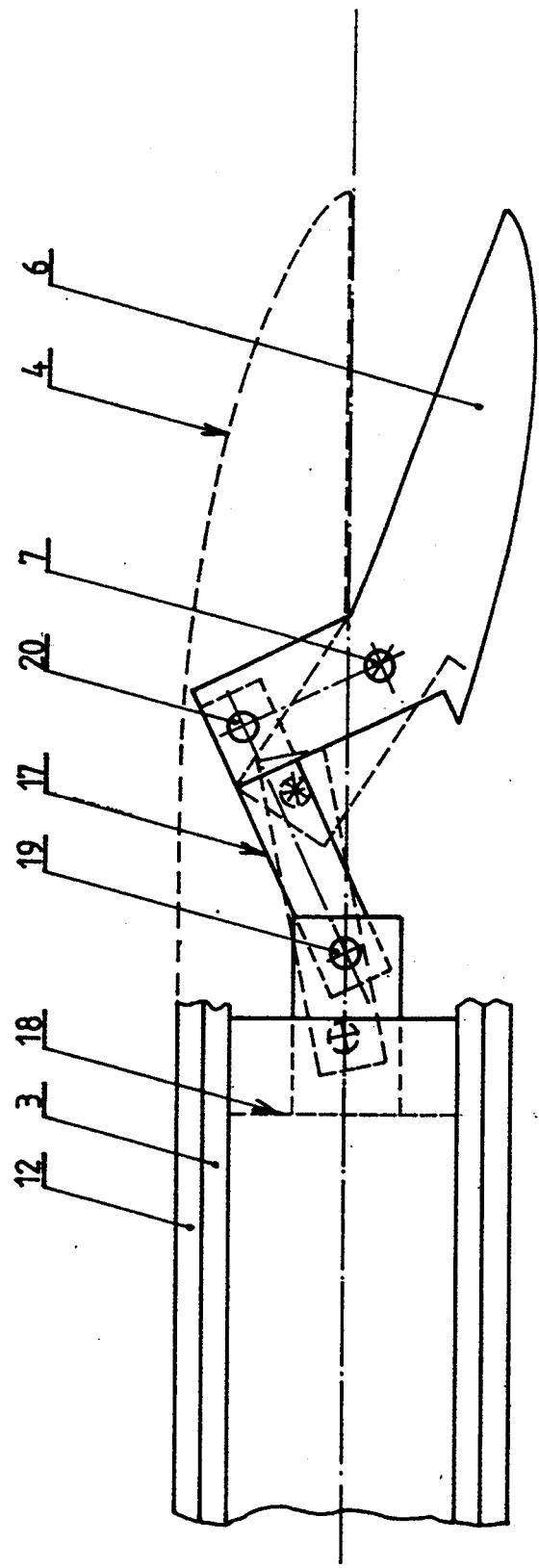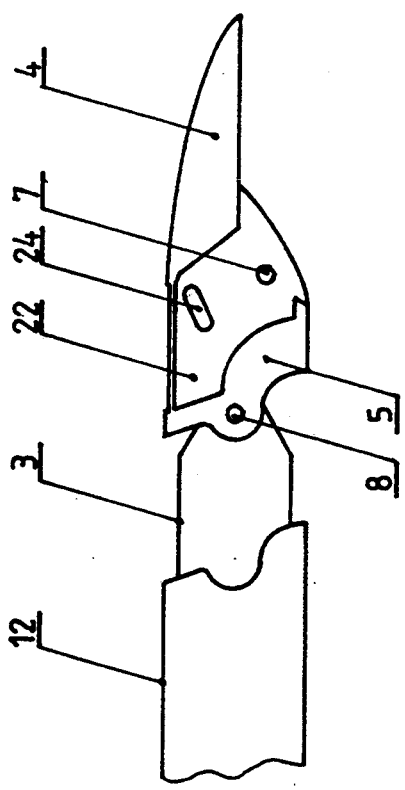
FIG._7_
FIG._10_

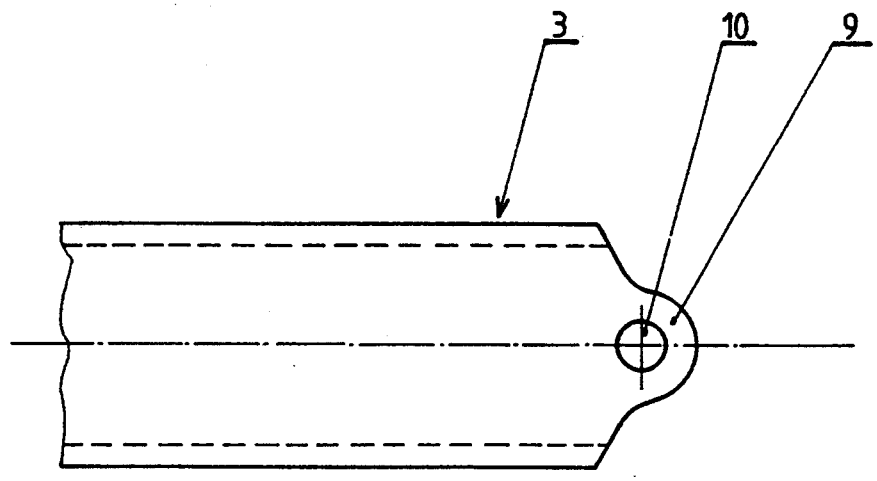
FIG_11.
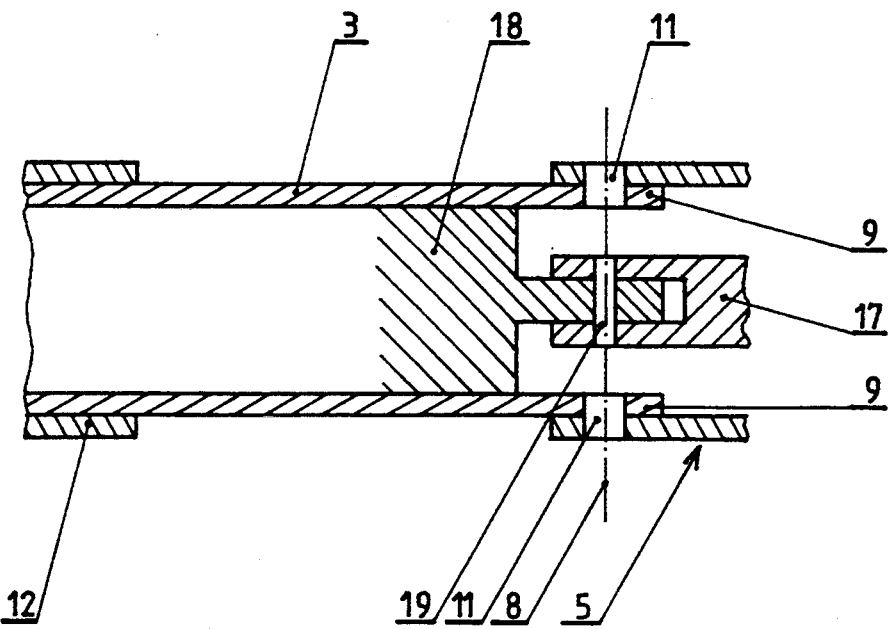
FIG_12.

COELIOSCOPIC ANGULATION FORCEPS

FIELD OF THE INVENTION

The present invention concerns forceps for use in coelioscopic surgery. In this type of surgery, the instruments used need to be introduced into trocars whose diameter is about 5 mm. These instruments are generally formed of a tube, a pair of jaws disposed at the distal extremity, and a pair of jaws control eyelets disposed at the proximal extremity via an activation rod mounted sliding inside said tube.

BACKGROUND OF THE INVENTION

This type of instrument can be used for various purposes, such as for carrying a suture needle, for carrying out the hemostatis of small vessels with the aid of suitable clamps, for carrying out a biopsy, etc.

Having regard to operational conditions, since the trocar in which the instrument is threaded is a fixed point on the abdominal wall, it is still impossible to have an optimal leading angle, even when orientating the instrument. In fact, there are locations which the instrument can hardly reach. Furthermore, these instruments are sometimes placed perpendicular to the viscus to be dissected when it would be necessary to be able to dissect perpendicular to this viscus.

Thus, the viscus is sometimes moved in order to be able to operate suitably, whereas on the contrary it is the instrument which needs to be adapted.

SUMMARY OF THE INVENTION

Accordingly, the invention seeks to provide forceps for coeliosurgery, with the distal portion of the forceps, namely the jaw holder, being able if required to be angled in situ, that is following introduction into the trocar, so as to allow for better access to the operating site.

With this aim in mind, the invention concerns angulation coelioscopic forceps including a tube, a pair of jaws at one extremity and a pair of eyelets at the other extremity of said tube connected to the pair of jaws via an activation rod assembly housed in said tube, to control positioning of the jaws relative to each other. The pair of jaws is borne by a jaw holder head pivotally joined to the extremity of said tube for rotation around an axis perpendicular to that of the tube and able to occupy two positions, one of which when the pair of jaws is an axial extension of the tube, and the other position where it forms a specific angulation with the axis of the tube. A device controls the positioning of the jaw holder head in either of said positions and is able to be activated from the proximal extremity of the tube.

According to one embodiment, said device for controlling the positioning of the jaw holder head is a sheath surrounding the tube and mounted mobile axially and in rotation with respect to the latter and whose distal extremity is adapted so that for two specific angular positions of said sheath, said jaw holder head is positioned in either of said positions.

In one version of the forceps with a fixed jaw and a mobile jaw in which the fixed jaw is integral with the jaw holder head, the mobile jaw is joined onto the fixed jaw and said head is joined onto said tube around an axis and, like the sheath, is adapted so that for two positions angularly offset by 180 degrees from the sheath, said fixed jaw takes up either of said two positions of the pair of jaws.

In this embodiment, the rods assembly for activating the jaws is formed of a rod mounted mobile in the tube and activated by said eyelets and connected to the mobile jaw by a rocker bar in prolongation of the rod and whose first hinge pin in the jaws rest position is approximately inside the plane perpendicular to the axis of the tube and containing the hinge pin of the jaw holder head on said tube.

Firstly, these forceps can be used in a straight position, that is with the pair of jaws in prolongation of the tubular body of the instrument, and secondly deliberately with the pair of jaws forming a bend of a specific angle, for example about fifteen degrees with respect to the axis of said tubular body, in the two positions, said jaws being able to be activated similarly with a given angle of opening.

The bent or elbowed placing of the distal extremity of the instrument is effected after insertion in a straight position in the trocar and then manipulation of the external sheath opposite to the proximal extremity, and thus accessible for the surgeon, of said tubular body so as to have the sheath move into its position angularly offset by 180 degrees, that is by making it tilt or rotate by a half-turn, so as to provide the general axis of the jaws with the desired angulation.

This type of instrument allows for improved access to the field of operation. It considerably opens the angle of intervention and makes it possible to more effectively position the active elements of the forceps, especially a suture needle or hemostatis clamps.

According to another characteristic of the device of the invention, the control eyelets are disposed at the extremity of two levers joined to the proximal extremity of the tube at two points symmetrical with respect to the axis of the tube and acting symmetrically by rocker bars on the extremity of the jaws activation rod. The forces on the activation rod are thus symmetrically distributed on both sides of the axis of the rod which is subjected rigorously and continuously to a coaxial component of forces, which ensures optimal accuracy and closing force of the forceps.

BRIEF DESCRIPTION OF THE DRAWINGS

Other characteristics and advantages shall appear more readily from a reading of the following description of an embodiment of the device of the invention, said description being given solely by way of example and with reference to the accompanying drawings on which:

FIG. 1 is a front lateral view of the extremity of the forceps of the invention is a straight rest position, FIG. 2 is a view of the other portion of the forceps, FIG. 3 shows the forceps of FIG. 1 with its sheath in a standing back position, FIG. 4 shows the sheath of FIG. 3 after rotation of one half-turn, FIG. 5 shows the forceps in the angulation position of the jaws holder, FIG. 6 shows the forceps of FIG. 1 in an opening position, FIG. 7 is a partial section of the device of FIG. 6, FIG. 10 shows the device of FIG. 3, the mobile jaw being removed, FIG. 11 is a lateral front view of the extremity of the tubular body of the forceps, and FIG. 12 is a partial axial cutaway view of the extremity of the forceps in the position of FIG. 3.

DETAILED DESCRIPTION OF THE INVENTION

Figure 8:
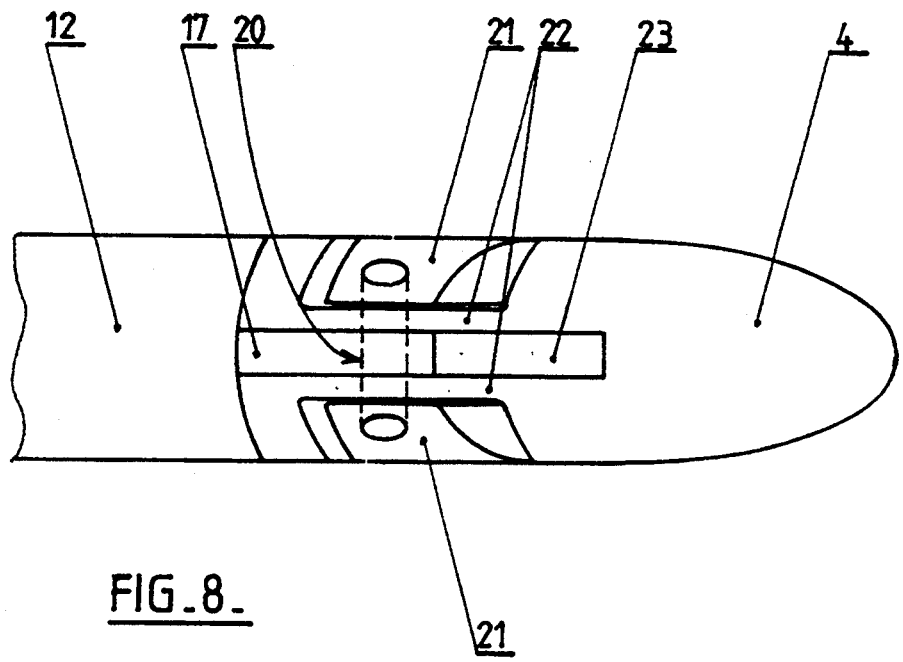
FIG. 8 is a bottom view of the device of FIG. 1.

The forceps shown on the drawings generally include a pair of jaws 1, a pair of control eyelets 2 and a tubular linking body 3, a device for activating the pair of jaws 1 being disposed in said body.

In this embodiment, the pair of jaws includes a fixed jaw 4 whose front portion constitutes a jaw holder head 5 and a mobile jaw 6 joined onto the fixed jaw 4 around a spindle 7 orthogonal to the axis of the tube or tubular body 3.

In accordance with the invention, the jaw holder head 5 is joined onto the extremity of the tube 3 around a spindle 8 perpendicular to the axis of the tube.

More specifically and as illustrated by FIGS. 11 and 12, the head 5 is tubular with a diameter slightly larger than that of the tube 3 so as to cover the latter or more specifically the two diametrical elongations 9 forming two eyes in which two holes 10 are fitted. The holes 10 receive pivots 11 for articulating the jaw holder head 5 around said spindle 8.

The head 5 may take up either position, as shown respectively on FIGS. 3 and 5, by means of a control device constituted by a sheath 12 sliding over the tube 3 and whose external diameter advantageously corresponds to that of the head 5. The distal extremity of the sheath 12 and the opposite extremity cooperating with the head 5 are adapted is such a way so that, according to two positions angularly offset by 180 degrees from the sheath 12 on the tube 3, the head 5 is forced to be positioned in either of two said positions.

To this effect, the head 5 is provided, opposite to the hinge pin 8, with projecting lugs 13 able to be engaged in two complementary notches 14 disposed diametrically opposite on the section of the sheath 12. Between the notches 14, the contour of the end section of the sheath 12 has one projecting cam portion 15 and one standing back cam portion 16, both being diametrical and charged to act on the section of the front extremity of the head 5 which is accordingly adapted so as to provide the head 5 with a specific amplitude angulation, such as 45 degrees, with respect to the axis of the tube 3, as shown on FIG. 5.

In the straight position (FIG. 1) of the forceps, the jaws 4 and 6 are closed and the general axis of the pair of jaws 1 is coaxial to the tube, the jaws and head 5 being profiled so as to ensure the continuity of the sheath 12. The extremity of the sheath is engaged against the head 5 in a first position of the cams 15 and 16.

By withdrawing the sheath 12 (FIG. 3) with respect to the head 5, the cams 15 and 16 and the notches 14 are disengaged and then the sheath is made to pivot by one half-turn around its axis (FIG. 4) and the extremity of the sheath is reapplied against the head 5.

The notches 14 resume their nesting position on the lugs 13 and the projecting cam 15 is made to tilt the head 5 around the spindle 8 until the standing back cam 16 abuts against the head 5 (FIG. 5). The pair of jaws 4 and 6 then takes up its maximum angulation position of about 45 degrees, for example, with respect to the axis of the tubular body 3 of the instrument. This position is stable since the head 5, as in the straight position, is locked in rotation around the spindle 8 by the opposing cams 15 and 16.

In the two positions of the head 5, the jaws may be activated, or more exactly the mobile jaw 6, in the same way and with approximately the same opening amplitude.

To this effect, the mobile jaw 6 is moved by a rocker bar 17 (FIGS. 5,12) articulated onto the extremity of an activation rod 18 around a spindle 19 perpendicular to the axis of the tube 3 and preferably approximately merged or coaxial in the jaws closing position with the hinge pin 8 of the head 5.

The rocker bar 17 is articulated onto the jaw 6 around a spindle 20.

Figure 9:
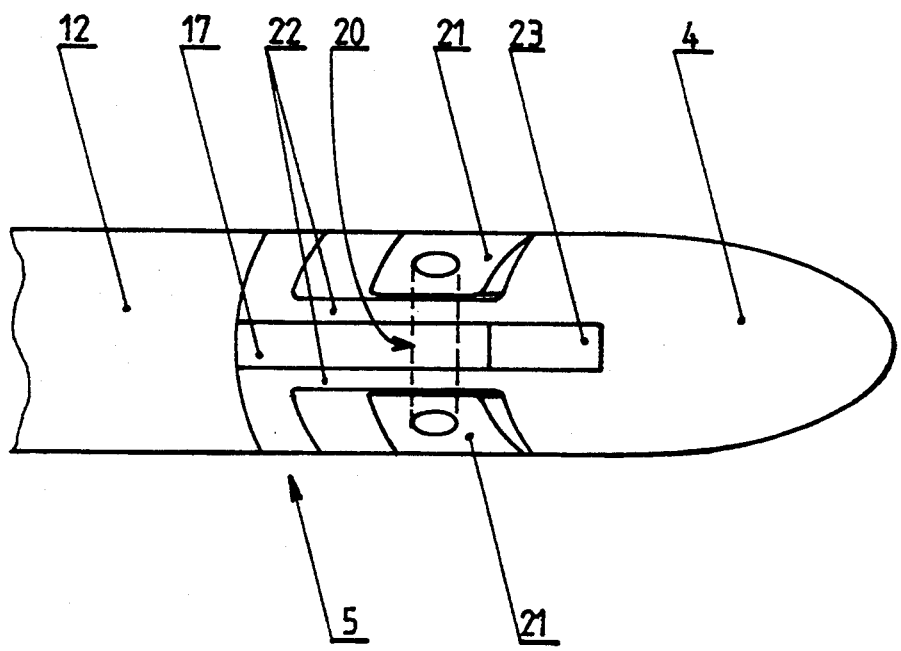
FIG. 9 is a top view of the device of FIG. 6.

The mobile jaw 6 has one front cap-shaped portion 21 attached astride on a central joining portion 22 of the head 5 to the fixed jaw 4 (FIGS. 8, 9, 10).

The rocker bar 17 moves into a central groove 23 fitted in the portion 22, the spindle 20 moving into slots 24 fitted (FIG. 10) in said portion 22.

FIG. 7 shows the two extreme positions of the rocker bar 17 resulting from an axial translation movement of the rod 18 inside the tube 3.

The other extremity of the rod 18 slides into an activating member holder plate 25 and is integral with a crosspiece 26. Two activating levers 27 are symmetrically articulated onto the plate 25 and connected to said crosspiece 26 through symmetrical rocker bars 28. On another hand, said activating levers 27 are articulated onto said plate 25 with respect to the axial plane of the instrument containing the hinge or pivoting pin 8 of the jaw holder head 5.

Finally, the sliding and rotation of the sheath 12 are provided manually and to this effect the proximal extremity of the sheath 12 is located close to the proximal extremity of the tubular body 12 and thus easily accessible by the operator when the instrument has been engaged in the trocar. This proximal extremity is fitted with a collar 29 for anchoring a spring 30 taking support at its other extremity against the plate 25. The sheath 12 is thus able to freely pivot on the tube 3 around its axis when the spring is compressed, and is constantly biased or forced toward a closed position by the spring 30, in the nesting position of the notches 14 on the lugs 13.

To provide the pair of jaws 4, 6 with the angulation permitted by the device, the sheath 12 (FIG. 3) is pulled towards the plate 25, compressing the spring 30 to remove lugs 13 from notches 14 so that the sheath can rotate by 180 degrees (FIG. 4). When the sheath is released, notches 14 are replaced on the lugs 13 (FIG. 5).

It is possible to fit on the sheath 12 and/or the plate 25 angular positioning marks of the sheath. Placing under the angulation of the extremity of the forceps and replacing it in a straight position is effected extremely easily with the instrument in place in a trocar.

It is to be noted that the jaw holder head 5 may be disposed to receive two mobile jaws able to open and close in synchronism and symmetrically with respect to the general axis of the head 5, the jaws then being suitably articulated onto the head and accordingly controlled by means of a device of the rudder-bar type.

In the embodiment with the fixed jaw 4 shown on the drawings, the general axis of the jaw holder head 5 is and remains (FIG. 7) approximately tangent to the active face of the jaw 4, whether the head is straight (FIG. 1) or inclined (FIG. 5).

According to one embodiment variant of the device shown, the spindle 7 for articulating the mobile jaw 6 onto the fixed jaw 4, instead of being parallel to the angulation spindle 8 of the jaw holder head 5, could be orthogonal to said spindle 8 or generally form any angle between 0 and 90 degrees with this spindle 8. This makes it possible to provide the jaws with an opening/closing plane which is not merged with the plane defined by the axes of the sheath 12 and the jaw holder head 5 in the angulation position (FIG. 5) of the forceps.

In this variant, the hinge pin 19 of the rocker bar 17 for controlling the mobile jaw 6 preferably remains in the jaws closing position approximately inside the plane containing the spindle 8 perpendicular to the axis of the tube 3.

Finally, the invention is not merely limited to the embodiment shown and described above, but on the contrary covers all possible variants, especially as regards the nature, shape and disposition of the jaws 4, 6, the disposition of the means for activating the latter and the disposition of the means fitted at the extremity of the sheath 12, so as to force the jaw holder head 5 to take up one of its two stable positions.

We claim:

1. A coelioscopic angulation forceps, comprising:
   a tube having first and second ends and a longitudinal axis;
   a jaw holder head pivotally coupled to said tube at said first end of said tube for acticulation about a pivot axis perpendicular to said tube longitudinal axis between first and second positions;
   first and second jaws coupled to said jaw holder head such that in said first position said jaws extend in a rest position along said longitudinal axis and in said second position said jaws extend in the rest position at a specific angle to said longitudinal axis;
   a pair of activating members at said second end of said tube;
   activating rod means, housed in said tube, for connecting said jaws and said activating members and actuating said jaws; and
   control means, engagable with said jaw holder head, for positioning said jaw holder head selectively in said first and second positions, said control means being activated adjacent said second end of said tube.

2. A coelioscopic angulation forceps according to claim 1 wherein
   said control means comprises a sheath surrounding said tube and being axially movable between first and second axial positions and rotatable relative to said tube between first and second angular positions, said sheath having first and second axial ends, said first axial end having positioning means for locating said jaw holder head in said first and second positions thereof when said sheath is in said first and second angular positions, respectively.

3. A coelioscopic angulation forceps according to claim 2 wherein
   said first jaw is integral with said jaw holder head;
   said second jaw is pivotally coupled to said first jaw;
   said jaw holder head comprises positioning means for mating with said positioning means of said sheath for locating said jaw holder head in said first and second positions thereof, respectively, by rotating said sheath by 180 degrees relative to said jaw holder head.

4. A coelioscopic angulation forceps according to claim 3 wherein
   said second jaw is pivotally coupled to said first jaw about an axis parallel to said pivot axis.

5. A coelioscopic angulation forceps according to claim 4 wherein
   said activating rod means comprises a rod movably mounted in said tube, said rod being activated by said activating members and connected to said second jaw by a rocker arm, said rocker arm extending generally axially from said rod; and
   a first hinge pin pivotally connects said rocker arm to said rod, said first hinge pin being substantially coaxial with said pivot axis in a closed position of said jaws.

6. A coelioscopic angulation forceps according to claim 3 wherein
   said activating rod means comprises a rod movably mounted in said tube, said rod being activated by said activating members and connected to said second jaw by a rocker arm, said rocker arm extending generally axially from said rod; and
   a first hinge pin pivotally connects said rocker arm to said rod, said first hinge pin being substantially coaxial with said pivot axis in a closed position of said jaws.

7. A coelioscopic angulation forceps according to claim 6 wherein
   said jaw holder head comprises a front tubular portion pivotally engaged with said tube; and
   said activating rod means extends through and moves in said front tubular portion.

8. A coelioscopic angulation forceps according to claim 2 wherein
   said jaw holder head comprises a front tubular portion pivotally engaged with said tube; and
   said activating rod means extends through and moves in said front tubular portion.

9. A coelioscopic angular forceps according to claim 1 wherein
   said jaw holder head comprises a front tubular portion pivotally engaged with said tube; and
   said activation rod means extends through and moves in said front tubular portion.

10. A coelioscopic angulation forceps according to claim 8 wherein
    said sheath is biased by a recall spring, adjacent said second axial end of said sheath, toward said jaw holder head.

11. A coelioscopic angulation forceps according to claim 6 wherein
    said sheath is biased by a recall spring, adjacent said second axial end of said sheath, toward said jaw holder head.

12. A coelioscopic angulation forceps according to claim 3 wherein
    said sheath is biased by a recall spring, adjacent said second axial end of said sheath, toward said jaw holder head.

13. A coelioscopic angulation forceps according to claim 2 wherein
    said sheath is biased by a recall spring, adjacent said second axial end of said sheath, toward said jaw holder head.

14. A coelioscopic angulation forceps according to claim 1 wherein
    each of said activating members is movable relative to said tube.

15. A coelioscopic angulation forceps according to claim 1 wherein each of said activating members is pivotally coupled to said tube.

16. A coelioscopic angulation forceps according to claim 1 wherein said activation rod means comprises a rigid rod axially slidable within said tube.

* * * * *